United States Patent
Cole-Yocom et al.

(10) Patent No.: US 10,773,210 B2
(45) Date of Patent: Sep. 15, 2020

(54) SYSTEMS AND METHODS FOR PURIFYING SOLVENTS

(71) Applicant: Fujifilm Electronic Materials U.S.A., Inc., North Kingstown, RI (US)

(72) Inventors: Marcia Cole-Yocom, Scottsdale, AZ (US); Bryan Hinzie, Gilbert, AZ (US); Jack Helzer, Chandler, AZ (US); Yuan Chen, Chandler, AZ (US); Pejman Ahmadiannamini, Gilbert, AZ (US)

(73) Assignee: Fujifilm Electronic Materials U.S.A., Inc., North Kingstown, RI (US)

( * ) Notice: Subject to any disclaimer, the term of this patent is extended or adjusted under 35 U.S.C. 154(b) by 0 days.

(21) Appl. No.: 16/684,769

(22) Filed: Nov. 15, 2019

(65) Prior Publication Data

US 2020/0156005 A1    May 21, 2020

Related U.S. Application Data

(60) Provisional application No. 62/769,612, filed on Nov. 20, 2018.

(51) Int. Cl.
| | |
|---|---|
| *B01D 61/00* | (2006.01) |
| *B01D 15/00* | (2006.01) |
| *C07C 45/78* | (2006.01) |
| *B01D 61/02* | (2006.01) |
| *B01D 61/08* | (2006.01) |
| *B01D 15/36* | (2006.01) |
| *B01D 71/36* | (2006.01) |
| *B01D 71/56* | (2006.01) |
| *C07C 67/48* | (2006.01) |
| *B01D 71/26* | (2006.01) |

(52) U.S. Cl.
CPC ......... *B01D 61/022* (2013.01); *B01D 15/361* (2013.01); *B01D 61/08* (2013.01); *B01D 71/26* (2013.01); *B01D 71/36* (2013.01); *B01D 71/56* (2013.01); *C07C 45/78* (2013.01); *C07C 67/48* (2013.01); *B01D 2311/25* (2013.01); *B01D 2311/2623* (2013.01)

(58) Field of Classification Search
CPC .... B01D 61/022; B01D 15/361; B01D 61/08; C07C 45/78; C07C 67/48
See application file for complete search history.

(56) References Cited

U.S. PATENT DOCUMENTS

| | | |
|---|---|---|
| 2003/0170945 A1 | 9/2003 | Igeta et al. |
| 2005/0170541 A1 | 8/2005 | Igeta et al. |
| 2015/0336195 A1 | 11/2015 | Kuramochi et al. |
| 2017/0184973 A1 | 6/2017 | Yamanaka |
| 2019/0308117 A1 | 10/2019 | Hinzie et al. |

FOREIGN PATENT DOCUMENTS

| | | | |
|---|---|---|---|
| JP | 2016-73922 | 5/2016 | ............. B01D 61/14 |
| WO | WO 2017/188296 | 11/2017 | ............ H01L 21/027 |
| WO | WO 2018/084302 | 5/2018 | ............. G03F 7/038 |

OTHER PUBLICATIONS

International Search Report and Written Opinion of the International Searching Authority for International Application No. PCT/US2019/061664 dated Jan. 30, 2020.

*Primary Examiner* — Sikarl A Witherspoon
(74) *Attorney, Agent, or Firm* — Fish & Richardson P.C.

(57) ABSTRACT

The present disclosure is directed to methods of purifying solvents. The purified solvents can be used for cleaning a semiconductor substrate in a multistep semiconductor manufacturing process.

30 Claims, 1 Drawing Sheet

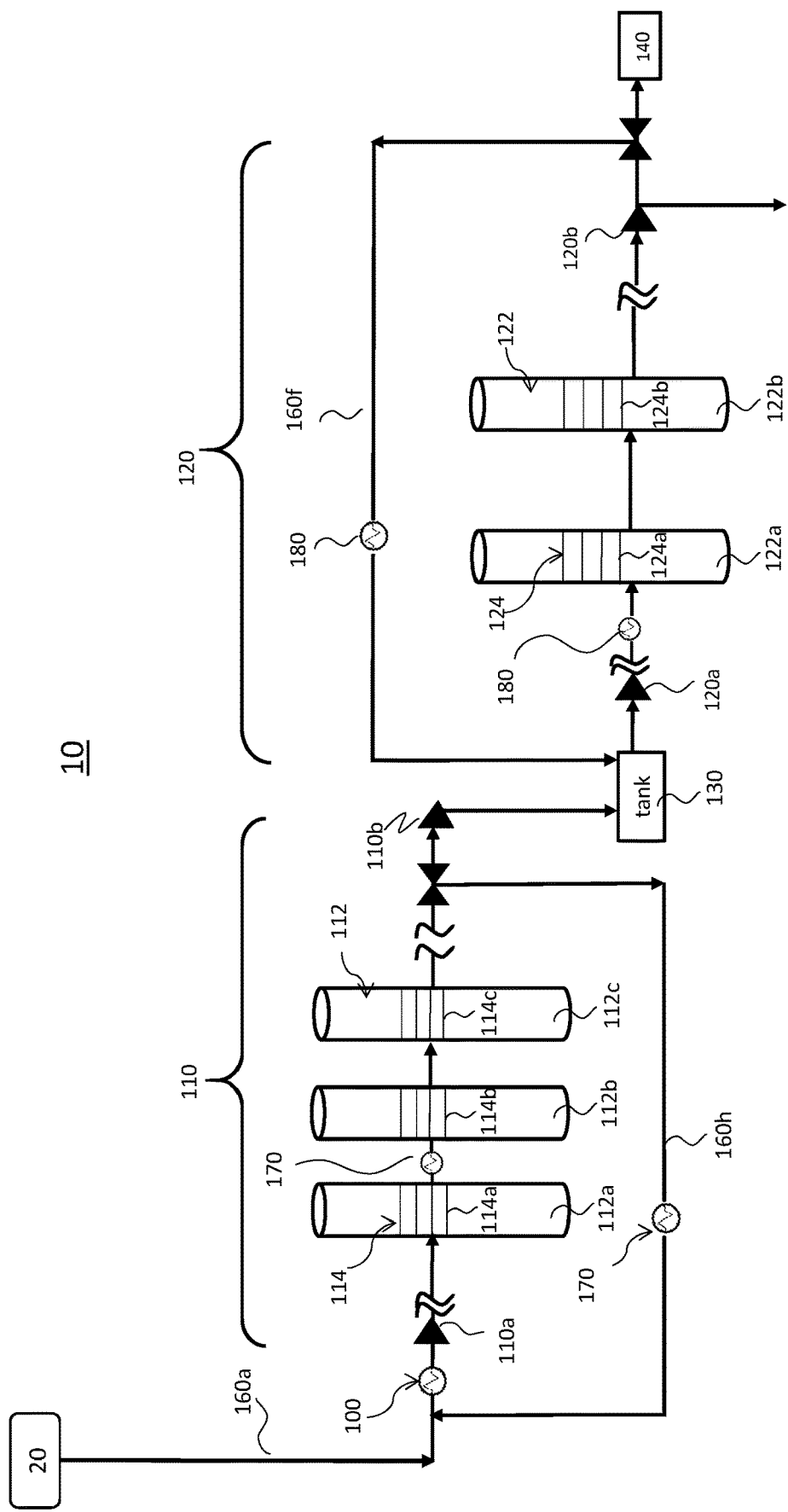

SYSTEMS AND METHODS FOR PURIFYING SOLVENTS

CROSS-REFERENCE TO RELATED APPLICATION

The present application claims priority to U.S. Provisional Application Ser. No. 62/769,612, filed on Nov. 20, 2018, the contents of which are hereby incorporated by reference in their entirety.

FIELD OF THE DISCLOSURE

The present disclosure relates to systems and methods for purifying solvents (e.g., organic solvents). In particular, the present disclosure relates to systems and methods that can be used to obtain organic solvents having a high purity, a low on wafer particle count, and a low on wafer metal count.

BACKGROUND OF THE DISCLOSURE

The semiconductor industry has achieved rapid improvements in integration density of electronic components, which are arisen from continuous reductions in the component size. Ultimately, more of the smaller components are afforded to be integrated into a given area. These improvements are mostly due to the development of new precision and high resolution processing techniques.

During the manufacturing of high resolution integrated circuits (ICs), various processing liquids will come into contact with a bare wafer or a film-coated wafer. For example, the fabrication of a fine metal interconnection typically involves a procedure of coating a base material with a pre-wetting liquid before the base material is coated with a composite liquid to form a resist film. These processing liquids, containing proprietary ingredients and various additives, are known to be a source of contamination of IC wafer.

One can speculate that even if a trace amount of contaminants is mixed into these chemical liquids, such as a wafer pre-wetting liquid or a developer solution, the resulting circuit patterns may have defects. It is known that the presence of very low levels of metal impurities, as low as 1.0 ppt, interferes with the performance and stability of semiconductor devices. And depending on the kind of metallic contaminants, oxide property can deteriorate, inaccurate patterns can be formed, electrical performance of semiconductor circuits can be impaired, which eventually adversely impact manufacturing yields.

The contamination of impurities, such as metal impurities, fine particles, organic impurities, moisture, and the like, can be inadvertently introduced in a chemical liquid during various stages of the manufacturing of the chemical liquid. Examples include a case where impurities are presented in a raw material, or a by-product generated or an unreacted reactant remained when the chemical liquid is manufactured, or foreign matters eluded or extracted from the surface of the manufacturing apparatus or from a container equipment, reaction vessels, or the like used in transporting, storing or reacting. Hence, a reduction or removal of insoluble and soluble contaminants from these chemical liquids used for the production of highly precise and ultra-fine semiconductor electronic circuits is a basic assurance of producing defective-free ICs.

In this respect, it is imperative to significantly improve and to rigorously control the standard and quality of chemical liquid manufacturing processes and systems in order to form high purity chemical liquids, which are indispensable in the fabrication of ultra-fine and immensely precise semiconductor electronic circuits.

SUMMARY OF THE DISCLOSURE

Accordingly, to form highly precise integrated circuits, the demands for ultra-pure chemical liquids, and the quality improvement and control of theses liquids become very critical. Specific key parameters targeted for quality improvement and control include: liquid and on-wafer metal reduction, liquid and on-wafer particle count reduction, on-wafer defect reduction, and organic contaminant reduction. All of these key parameters are shown to be impacted by a requisite preparation of a purification system and a proper design of a purification process.

In view of the above, the present disclosure is to provide particularly a purification system and a method of purifying a solvent (e.g., an organic solvent) using the same for preparing a solvent targeted for semiconductor manufacturing, wherein an ultra-pure solvent is produced with the number of particulates and the amount of metallic impurities in the solvent managed within predetermined ranges and without the generation or introduction of unknown and unwanted substances. Hence, the occurrence of residue and/or particle defects is suppressed and the yield of semiconductor wafer is improved.

In one aspect, the disclosure features a method of purifying an organic solvent that includes passing an organic solvent through a first filter to a packaging station in a purification system to obtain a purified organic solvent. The first filter includes a filter housing and at least one filtration medium within the filter housing, and the at least one filtration medium has an average pore size of at most about 5 nm. The purification system includes the first filter, the packaging station, and a conduit in fluid communication with the first filter and the packaging station, and the inner surface of the conduit or the filter housing includes a fluoropolymer.

In another aspect, the disclosure features a method of purifying an organic solvent that includes passing an organic solvent through first and second filters to obtain a purified organic solvent. The first filter includes at least one filtration medium that has an average pore size of at most about 5 nm and includes a polyamide, and the second filter includes at least one filtration medium that has an average pore size of at most about 5 nm and includes a fluoropolymer.

In another aspect, the disclosure features a system that includes (1) a first filter that includes a filter housing and at least one filtration medium within the filter housing, and the at least one filtration medium has an average pore size of at most about 5 nm; (2) a packaging station; and (3) a conduit in fluid communication with the first filter and the packaging station. The inner surfaces of the filter housing and the conduit includes a fluoropolymer.

In still another aspect, the disclosure features a system that includes (1) a first filter that includes a filter housing and at least one filtration medium within the filter housing, in which the at least one filtration medium has an average pore size of at most about 5 nm and includes a polyamide; and (2) a second filter in fluid communication with the first filter, in which the second filter includes a filter housing and at least one filtration medium within the filter housing, and the at least one filtration medium has an average pore size of at most about 5 nm and includes a fluoropolymer.

Embodiments can include on or more of the following features.

In some embodiments, the methods described herein can further include passing the organic solvent through a second filter in fluid communication with and between the first filter and packaging station, wherein the second filter includes a filter housing and at least one filtration medium within the filter housing, and the at least one filtration medium in the second filter has an average pore size of at most about 5 nm. In some embodiments, the inner surface of the filter housing of the second filter can include a fluoropolymer. In some embodiments, the entire second filter can be made of a fluoropolymer.

In some embodiments, the at least one filtration medium in the first or second filter includes a polyamide (e.g., a nylon), a polyolefin (e.g., a polyethylene), a fluoropolymer (e.g., a polytetrafluoroethylene), or a copolymer thereof. For example, the at least one filtration medium in the first filter can include a nylon and the at least one filtration medium in the second filter can include a polytetrafluoroethylene.

In some embodiments, the fluoropolymer in the inner surface of the first filter, the second filter, or the conduit can include a polytetrafluoroethylene or a copolymer thereof.

In some embodiments, the first filter can include 1 to 120 filtration media and the second filter can include 1 to 30 filtration media.

In some embodiments, passing the organic solvent through the first filter to the packaging station is performed at a temperature of at most about 80° F.

In some embodiments, the methods described herein can further include passing the organic solvent through a heat exchanger to maintain the temperature of the organic solvent at most about 80° F.

In some embodiments, the methods described herein can further include passing the organic solvent through a third filter before passing the organic solvent through the first filter, wherein the third filter includes at least one filtration medium that has an average pore size of at most about 200 nm. In some embodiments, the methods described herein can further include passing the organic solvent through a fourth filter after passing the organic solvent through the third filter but before passing the organic solvent through the first filter, wherein the fourth filter includes at least one ion exchange filtration medium. In some embodiments, the methods described herein can further include passing the organic solvent through a fifth filter after passing the organic solvent through the fourth filter but before passing the organic solvent through the first filter, wherein the fifth filter includes at least one filtration medium that has an average pore size of at most about 20 nm.

In some embodiments, the methods described herein can further include circulating the organic solvent through a recirculation loop that includes the first filter at least two times before passing the organic solvent to the packaging station.

In some embodiments, the organic solvent comprises cyclohexanone, ethyl lactate, n-butyl acetate, propylene glycol methyl ether, propylene glycol methyl ether acetate, 4-methyl-2-pentanol, or propylene carbonate.

BRIEF DESCRIPTION OF THE DRAWING

FIG. 1 is a schematic diagram showing an example of a purification system adopted in a method of purifying an organic solvent in accordance with some embodiments of the present disclosure.

DETAILED DESCRIPTION OF THE DISCLOSURE

As defined herein, unless otherwise noted, all percentages expressed should be understood to be percentages by weight to the total weight of a composition. Unless otherwise noted, ambient temperature is defined to be between about 16 and about 27 degrees Celsius (° C.). The term "solvent" mentioned herein, unless otherwise noted, refers to a single solvent or a combination of two or more (e.g., three or four) solvents. In the present disclosure, "ppm" means "parts-per-million", "ppb" means "parts-per-billion" and "ppt" means "parts-per-trillion".

In general, the disclosure features systems and methods for purifying a solvent (e.g., an organic solvent). The solvent mentioned herein can be used as a wafer processing solution (such as a pre-wetting liquid, a developer solution, a rinsing solution, a cleaning solution, or a stripping solution), or a solvent for a semiconductor material used in a semiconductor manufacturing process.

Prior to being subjected to a purification method of the present disclosure, a solvent may contain an undesirable amount of contaminants and impurities. After the solvent is processed by the purification method of the present disclosure, substantial amounts of the contaminants and impurities can be removed from the solvent. A pre-processed solvent is also referred herein in the present disclosure as an "unpurified solvent". The pre-processed solvent can be synthesized in house or commercially available via purchasing from a supplier. A post-processed solvent is also referred in the present disclosure as a "purified solvent". A "purified solvent" may include impurities limited within predetermined ranges.

In general, the solvent mentioned herein can include at least one (e.g., two, three, or four) organic solvent. Examples of suitable organic solvents include methanol, ethanol, 1-propanol, isopropanol, n-propanol, 2-methyl-1-propanol, n-butanol, 2-butanol, tert-butanol, 1-pentanol, 2-pentanol, 3-pentanol, n-hexanol, cyclohexanol, 2-methyl-2-butanol, 3-methyl-2-butanol, 2-methyl-1-butanol, 3-methyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 2-ethyl-1-butanol, 2,2-dimethyl-3-pentanol, 2,3-dimethyl-3-pentanol, 2,4-dimethyl-3-pentanol, 4,4-dimethyl-2-pentanol, 3-ethyl-3-heptanol, 1-heptanol, 2-heptanol, 3-heptanol, 2-methyl-2-hexanol, 2-methyl-3-hexanol, 5-methyl-1-hexanol, 5-methyl-2-hexanol, 2-ethyl-1-hexanol, methyl cyclohexanol, trimethyl cyclohexanol, 4-methyl-3-heptanol, 6-methyl-2-heptanol, 1-octanol, 2-octanol, 3-octanol, 2-propyl-1-pentanol, 2,6-dimethyl-4-heptanol, 2-nonanol, 3,7-dimethyl-3-octanol, ethylene glycol, propylene glycol, diethyl ether, dipropyl ether, diisopropyl ether, butyl methyl ether, butyl ethyl ether, butyl propyl ether, dibutyl ether, diisobutyl ether, tert-butyl methyl ether, tert-butyl ethyl ether, tert-butyl propyl ether, di-tert-butyl ether, dipentyl ether, diisoamyl ether, cyclopentyl methyl ether, cyclohexyl methyl ether, bromomethyl methyl ether, α,α-dichloromethyl methyl ether, chloromethyl ethyl ether, 2-chloroethyl methyl ether, 2-bromoethyl methyl ether, 2,2-dichloroethyl methyl ether, 2-chloroethyl ethyl ether, 2-bromoethyl ethyl ether, (±)-1,2-dichloroethyl ethyl ether, 2,2,2-trifluoroethyl ether, ethyl vinyl ether, butyl vinyl ether, allyl ethyl ether, allyl propyl ether, allyl butyl ether, diallyl ether, 2-methoxypropene, ethyl-1-propenyl ether, cis-1-bromo-2-ethoxyethylene, 2-chloroethyl vinyl ether, allyl-1,1,2,2-tetrafluoroethyl ether, octane, isooctane, nonane, decane, methylcyclohexane, decalin, xylene, ethylbenzene, diethylbenzene, cumene, second-butylbenzene, cymene, dipentene, methyl pyruvate, monomethyl ether, propylene glycol monomethyl ether, propylene glycol monoethyl ether, propylene glycol monopropyl ether, propylene glycol monomethyl ether acetate, ethyl lactate, methyl methoxypropionate, cyclopentanone, cyclohexanone, n-butyl acetate, γ-butyrolactone, diisoamyl ether, isoamyl acetate, chloroform, dichloromethane, 1,4-dioxane, hexyl alcohol, 2-heptanone, isoamyl acetate, propylene carbonate, and tetrahydrofuran.

In some embodiments, the solvent is a pre-wetting liquid. Examples of a pre-wetting liquid include at least one of cyclopentanone (CyPe), cyclohexanone (CyH), monomethyl ether, propylene glycol monomethyl ether (PGME), propylene glycol monoethyl ether (PGEE), propylene glycol monomethyl ether acetate (PGMEA), propylene glycol monopropyl ether (PGPE), and ethyl lactate (EL). In other embodiments, the solvent can be a developer solution such as n-butyl acetate, or a rinsing liquid such as 4-methyl-2-pentanol (MIBC).

In some embodiments, the pre-processed or unpurified organic solvent can have a purity of at least about 95% (e.g., at least about 96%, at least about 97%, at least about 98%, or at least about 99%). In some embodiments, the post-processed or purified organic solvent obtained from the methods described herein can have a purity of at least about 99.5% (e.g., at least about 99.9%, at least about 99.95%, at least about 99.99%, at least about 99.995%, or at least about 99.999%). As mentioned herein, "purity" refers to the weight percentage of the solvent in the total weight of the liquid. The content of the organic solvent in a liquid can be measured by using a gas chromatography mass spectrometry (GCMS) device.

In some embodiments, the boiling point of the solvent described herein is at most about 200° C. (e.g., at most about 150° C.) or at least about 50° C. (e.g., at least about 100° C.) from a point of improving manufacturing yield of a semiconductor chip. In this disclosure, the boiling point means a boiling point at 1 atm.

In general, impurities contained in a pre-processed organic solvent can include metallic impurities, particles, and others such as organic impurities and moisture.

As described herein, metal impurities can be in a form of a solid (e.g., metal simplex, particulate metal-containing compound, and the like). Examples of common metallic impurities include heavy metals such as iron (Fe), aluminum (Al), chromium (Cr), lead (Pb), and nickel (Ni), and ionic metals such as sodium (Na), potassium (K), and calcium (Ca). Depending on the type of metal, metal impurities can deteriorate oxide integrity, degrade MOS gate stacks, and reduce lifetime of devices. In an organic solvent purified by the methods described herein, the total trace metal content is preferred to be within a predetermined range of 0 to 300 ppt (e.g., 0 to 150 ppt) in mass.

In the present disclosure, substances having a size of 0.03 μm or greater are referred to as "particles" or "particulates". Examples of particles include dust, dirt, organic solid matters, and inorganic solid matters. The particles can also include impurities of colloidalized metal atoms. The type of the metal atoms that are easily colloidalized is not particularly limited, and can include at least one metal atom selected from the group consisting of Na, K, Ca, Fe, Cu, Mg, Mn, Li, Al, Cr, Ni, Zn, and Pb. In an organic solvent purified by the methods described herein, the total number of the particles having a size of 0.03 μm or more is preferred to be within a predetermined range of at most 100 (e.g., at most 80, at most 60, at most 50, at most 40, or at most 20) per 1 ml of the solvent. The number of "particles" in a liquid medium are to be countered by a light scattering type in-liquid particle counter and is referred as LPC (liquid particle count).

As described herein, organic impurities are different from the organic solvent and refer to organic matters that are contained in the content of 5000 mass ppm or smaller with respect to the total mass of the liquid containing the organic solvent and the organic impurities. Organic impurities can be volatile organic compounds that are present in ambient air even inside a clean-room. Some of the organic impurities originate from the shipping and storage equipment, while some are presented in a raw material from the start. Other examples of organic impurities include a by-product generated when the organic solvent is synthesized and/or an unreacted reactant.

The total content of the organic impurities in a purified organic solvent is not particularly limited. From a point of improving the manufacturing yield of a semiconductor device, the total content of the organic impurities can be 0.1 to 5000 mass ppm (e.g., 1 to 2000 mass ppm, 1 to 1000 mass ppm, 1 to 500 mass ppm, or 1 to 100 mass ppm) in a purified organic solvent. The content of the organic impurities in the solvent described herein can be measured by using a gas chromatography mass spectrometry (GC-MS) device.

FIG. 1 is a schematic diagram showing a configuration of a purification system according to some embodiments of the present disclosure. As shown in FIG. 1, the purification system 10 includes a supply unit 20, a first filtration system 110, a storage tank 130, a second filtration system 120, and a package station 140, all of which are in fluid communication with each other (e.g., through one or more conduits).

In general, supply unit 20 (e.g., a tank) is configured to hold or transport a starting material (e.g., a pre-processed or unpurified organic solvent). The starting material can be processed by purification system 10 to produce or manufacture a purified organic solvent in which the number of unwanted contaminants (e.g., particulates, organic impurities, metallic impurities) are limited within predetermined ranges. The type of supply unit 20 is not particularly limited as long as it continuously or intermittently supplies the starting material to the other components of purification system 10. In some embodiments, supply unit 20 can include a material receiving tank, a sensor such as a level gauge (not shown), a pump (not shown), and/or a valve for controlling the flow of the starting material (not shown). In FIG. 1, purification system 10 includes one supply unit 20. However, in some embodiments, a plurality of supply units 20 can be provided (e.g., in parallel or series) for each type of starting materials to be processed by purification system 10.

Purification system 10 can include at least one first filtration system 110 and at least one second filtration system 120. In general, first filtration system 110 performs an initial filtration of the starting material (e.g., unpurified organic solvent) to remove the majority of the impurities and/or particles, and second filtration system 120 performs a subsequent filtration to remove the remaining impurities and fine particles to obtain a ultra-high purity organic solvent.

In some embodiments, purification system 10 can optionally include a temperature control unit 100 for setting or maintaining the temperature of the organic solvent within a certain temperature range such that the organic solvent is maintained at a substantially consistent temperature during the purification process. As described herein, a temperature control unit can include, but are not limited to, a commercial recirculating heating/cooling unit, a condenser, or a heat exchanger, which can be installed, for example, on a conduit in purification system 10. Temperature control unit 100 can be configured, for example, between supply unit 20 and the first filtration system 110. In some embodiments, temperature control unit 100 can set the temperature of the organic solvent to at most about 80° F. (e.g., at most about 75° F., at most about 70° F., at most about 65° F., or at most about 60° F.) or and/or at least about 30° F. (e.g., at least about 40° F., at least about 50° F., or at least about 60° F.). In some embodiments, because pumps used in purification system 10 can generate heat and increase solvent temperature, purification system 10 can include additional temperature control unit (such as units 170 and 180 described below) at suitable locations to maintain the temperature of the solvent at a predetermined value.

Referring to FIG. 1, first filtration system 110 can include an optional temperature control unit 100, a supply port 110a, one or more (e.g., two, three, four, five, or ten) filters 112, an outflow port 110b, an optional recirculation conduit 160h, and one or more optional temperature control units 170, all of which are in fluid communication with each other (e.g., through one or more conduits).

In some embodiments, each filter 112 can include a filter housing and one or more filtration media 114 in the filter housing. For example, first filtration system 110 shown in FIG. 1 includes three filters (i.e., 112a, 112b, and 112c), each of which includes one or more filtration media 114a, 114b, and 114c, respectively. In some embodiments, filters 112 may not have separate housings, and the one or more filtration media 114 (e.g., 114a, 114b, or 114c) are configured un-compartmentalized in first filtration system 110. In other embodiments, first filtration system 110 can also include other purification modules (not shown) in addition to the one or more filters 112.

Referring to FIG. 1, filter 112a can include one or more filtration media 114a, filter 112b can include one or more filtration media 114b, and filter 112c can include one or more filtration media 114c, in which filtration media 114a, 114b and 114c can be different in functionality or property and offer different purification treatments. In some embodiments, certain filtration media 114 (e.g., 114a, 114b, and 114c) accommodated within the corresponding filters 112 (e.g., 112a, 112b, and 112c), respectively, can have the same or similar purification function, physiochemical properties, pore size and/or construction material. In some embodiments, each filter 112 can independently be selected from the group consisting of a particle removal filter, an ion exchange filter, and an ion absorption filter.

In some embodiments, filtration media 114a in filter 112a can be particle removal filtration media to remove relative large particles from the organic solvent. In some embodiments, filtration media 114a can have an average pore size of at most about 1000 nm (e.g., at most about 800 nm, at most about 600 nm, at most about 500 nm, at most about 400 nm, at most about 200, or at most about 150 nm) and/or at least about 50 nm (e.g., at least about 100 nm, at least about 150 nm, at least about 200 nm, or at least about 250 nm). Within the above range, it is possible to reliably remove foreign matters such as impurities or aggregates contained in the organic solvent while suppressing clogging of a subsequent filter (e.g., filter 112b, 112c, 122a, or 122b). In some embodiments, filter 122a can include one, two, three, four, five, six, and seven filtration media 114a.

Examples of suitable materials of the particle removal filter include a fluoropolymer (e.g., polytetrafluoroethylene (PTFE), perfluoroalkoxy alkane (PFA), or a modified polytetrafluoroethylene (MPTFE)), a polyamide resin such as nylon (e.g., nylon 6 or nylon 66), a polyolefin resin (including high density and ultrahigh molecular weight) such as polyethylene (PE) and polypropylene (PP). For example, the filtration medium in a particle removal filter can be made of at least one polymer selected from the group consisting of a nylon, a polypropylene (including high density polypropylene), a polyethylene, a polytetrafluoroethylene, a tetrafluoroethylene-perfluoroalkyl vinyl ether copolymer, a polyimide, and a polyamide imide. A filter made of the above material can effectively remove foreign matters (e.g., those having high polarity) which are likely to cause residue defects and/or particle defects, and to efficiently reduce the content of the metal components in the chemical liquid.

In some embodiments, filtration media 114b in filter 112b can be ion exchange resin membranes to remove charged particles and/or metal ions from the organic solvent. The ion-exchange resin membrane used in the present disclosure is not particularly limited, and filters including an ion exchange resin having a suitable ion-exchange group immobilized to a resin membrane can be used. Examples of such ion-exchange resin membranes include strongly acidic cation-exchange resins having a cation-exchange group (such as a sulfonic acid group) chemically modified on the resin membrane. Examples of suitable resin membranes include those containing cellulose, diatomaceous earth, nylon (a resin having an amide group), polyethylene, polypropylene, polystyrene, a resin having an imide group, a resin having an amide group and an imide group, a fluororesin, or a high-density polyethylene membrane. In some embodiments, the ion-exchange resin membrane can be a membrane having an integral structure of a particle-removing membrane and an ion-exchange resin membrane. Polyalkylene (e.g., PE or PP) membranes with an ion-exchange group chemically modified thereon are preferred. Cation-exchange groups are preferred as the ion-exchange group. Filters with ion-exchange resin membranes used in the present disclosure can be commercially available filters with metal ion removal functionality. These filters can be selected based on the ion exchange efficiency and with an estimated pore size of the filters as small as about 0.2 μm (200 nm).

In some embodiments, filtration media 114c in filter 112c can be ion absorption membranes to remove relative small particles and/or metal ions from the organic solvent. An ion adsorption membrane can have a porous membrane material and can have an ion exchange function. Examples of suitable materials that can be used to make an ion adsorption membrane include, but are not limited to, cellulose, diatomaceous earth, film materials of microfiltration membranes such as nylon (resin having amide group), polyethylene (e.g., high density polyethylene), polypropylene, polystyrene, resins having imide group, resins having amide group and imide group, fluororesins, membrane materials having an ion exchange ability functional group introduced therein, or the like. Examples of the shape of the membrane material include a pleated type, a flat membrane type, a hollow fiber type, a porous body as described in JP-A No. 2003-112060 and the like. As the ion exchange group to be introduced into the membrane material, it is preferable to use a combination of at least two of the cation exchange group, the chelate exchange group, and the anion exchange group to optimize the elution and selectivity of the components to be removed. Since the ion adsorption membrane has porosity, it is also possible to remove a part of the fine particles.

In some embodiments, filtration media 114c can have an average pore size of at most about 100 nm (e.g., at most about 80 nm, at most about 60 nm, at most about 50 nm, at most about 40 nm, at most about 20, or at most about 15 nm) and/or at least about 5 nm (e.g., at least about 10 nm, at least about 15 nm, at least about 20 nm, or at least about 25 nm).

Without wishing to be bound by theory, it is believed that the ability of first filtration system 110 to remove impurities can be optimized by using filters having different medium types and different pore sizes. For example, in such a first filtration system 110, filter 112a can be a filter having one or more polypropylene media with an average pore size of about 200 nm, filter 112b can be an ion exchange filter, and filter 112c can be a filter having one or more nylon media with an average pore size of about 20 nm.

In some embodiments, first filtration system 110 can optionally include a recirculation conduit 160h to form a recirculation loop for recirculating a partially-purified organic solvent back to first filtration system 110 and to be processed by the filters in first filtration system 110 again. In some embodiments, a temperature control unit 170 (e.g., a heat exchanger) can be configured along recirculation conduit 160h. In such embodiments, temperature control unit 170 can be configured at a temperature of at most about 80° F. (e.g., at most about 75° F., at most about 70° F., or at most about 65° F.) and/or at least about 30° F. (e.g., at least about 40° F., at least about 50° F., or at least about 60° F.) so that the temperature of the partially-purified organic solvent is maintained at about 80° F. or below as it is being recirculated back to first filtration system 110. In the examples as shown in FIG. 1, recirculation conduit 160h is configured at the upstream side of outflow port 110b of first filtration system 110. In some embodiments, recirculation conduit 160h can be configured at the downstream side of outflow port 110b. It is understood that pumps and valves may be installed at the various conduits, outflow ports and supply ports, supply unit 20, and temperature control unit 100 of first filtration system 110 as necessary.

As in the examples illustrated in FIG. 1, purification system 110 can optionally include a temperature control unit 170 (e.g., a heat exchanger) configured between filter 112a and filter 112b to control the temperature of the organic solvent to at most about 80° F. (e.g., at most about 75° F., at most about 70° F., or at most about 65° F.) and/or at least about 30° F. (e.g., at least about 40° F., at least about 50° F., or at least about 60° F.) before the organic solvent is charged into and processed in filter 112b.

It should be noted also that the position of temperature control unit 170 is not limited to the examples shown above. In some embodiments, a temperature control unit 170 can be configured upstream of filter 112a, between filters 112b and 112c, or downstream of filter 112c. In such embodiments, another temperature control unit may or may not be installed downstream of filter 112a prior to the entry of subsequent filters (e.g., filter 112b and/or filter 112c). Configuring another temperature control unit downstream of filter 112a is optional provided that no other means or equipment (e.g., a pump), which may re-introduce thermal energy into the organic solvent, is introduced or disposed between filter 112a and the subsequent filters (e.g., filter 112b or 112c).

In some embodiments, filters 112 in first filtration system 110 may not include filter housings, and the one or more filtration media 114 are configured un-compartmentalized in first filtration system 110. For example, first filtration system 110 can be a multistage system including replaceable filtration media 114 (e.g., 114a, 114b, and 114c) that are concatenated together inside first filtration system 110, and the organic solvent can be caused to cascade through filtration media 114 (e.g., 114a, 114b, and 114c). In such embodiments, a temperature control unit 170 can be configured at any position upstream of a first ion exchange membrane or ion adsorption membrane through which the organic solvent passes or cascades. For example, if first filtration system 110 houses, in sequence and downstream of its supply port 110a, particle removal filter A, particle removal filter B, ion exchange membrane A, ion exchange membrane B, and an ion adsorption membrane A, a temperature control unit 170 may be configured between particle removal filter B and ion exchange membrane A to have the temperature of the organic solvent adjusted and regulated to about 80° F. or below before the organic solvent passes through and is processed by the ion exchange membrane A, and by the subsequent ion exchange membrane B and an ion adsorption membrane A. It is noted that the above examples are for illustrative purposes and are not intended to be limiting.

As shown in FIG. 1, purification system 10 also includes a second filtration system 120, which is in fluid communication with and between storage tank 130 and packaging station 140. Second filtration system 120 can include a supply port 120a, one or more (e.g., two, three, four, five, or ten) filters 122, an outflow port 120b, a recirculation conduit 160f, and one or more optional temperature control units 180, all of which are in fluid communication with each other (e.g., through one or more conduits). It is understood that pumps and valves may be installed at the various conduits, outflow ports and supply ports, and temperature control units in second filtration system 120 as necessary.

In some embodiments, each filter 122 can include a filter housing and one or more filtration media 124 in the filter housing. For example, second filtration system 120 shown in FIG. 1 includes two filters (i.e., 122a and 122b), each of which includes one or more filtration media 124a and 124b, respectively. In some embodiments, second filtration system 120 can include only one filter (e.g., 122a). In some embodiments, filters 122 may not have separate housings, and the one or more filtration media 124 (e.g., 124a and 124b) are configured un-compartmentalized in second filtration system 120. In other embodiments, second filtration system 120 can also include other purification modules (not shown) in addition to the one or more filter 122.

Referring to FIG. 1, filter 122a can include one or more filtration media 124a, and filter 122b can include one or more filtration media 124b, in which filtration media 124a and 124b can be different in functionality or property and offer different purification treatments. In some embodiments, filtration media 124 (e.g., 124a and 124b) accommodated within each of the corresponding filters 122 (e.g., 122a and 112b), respectively, can have the same or similar purification function, physiochemical properties, pore size and/or construction material. In some embodiments, each filter 122 can independently be selected from the group consisting of a particle removal filter, an ion exchange filter, and an ion absorption filter.

In some embodiments, filtration media 124a in filter 122a can be ion absorption membranes (such as those described above with respect to filtration media 114c) to remove fine charged particles and/or metal ions in the organic solvent to be purified. In some embodiments, filtration media 124a can have an average pore size of at most about 10 nm (e.g., at most about 7 nm, at most about 5 nm, at most about 3 nm, or at most about 1 nm) and/or at least about 1 nm (e.g., at least about 3 nm, or at least about 5 nm). It is believed that filtration media 124a can both perform sieving functions (e.g., to remove fine particles) and ion-exchange functions (e.g., to remove charged particles and/or metal ions).

Examples of suitable materials that can be used in filtration media 124a or 124b include a polyamide (e.g., nylon such as nylon 6 or nylon 66), a polyolefin (e.g., a polyethylene or a polypropylene), a fluoropolymer (e.g., a polytetrafluoroethylene (PTFE), perfluoroalkoxy alkane (PFA), or a modified polytetrafluoroethylene (MPTFE)), or a copolymer thereof. In some embodiments, filtration media 124a or 124b can be made from a non-fluoropolymer, such as a polyamide (e.g., a nylon).

In some embodiments, filter 122a can include at least one (e.g., at least 2, at least 3, at least 5, at least 10, at least 20, at least 30, at least 50, or at least 80) and/or at most 120 (e.g., at most 110, at most 100, at most 90, at most 70, at most 50, or at most 25) filtration media 124a.

In some embodiments, filtration media 124b (e.g., ion absorption membranes) in filter 122b can have the same characteristics (e.g., the same pore size) as filtration media 124a in filter 122a except that they are made from a different material. For example, in some embodiments, when filtration media 124a in filter 122a is made from a nylon, filtration media 124b in filter 122b can be made from a fluoropolymer (e.g., a PTFE). In some embodiments, filter 122b can include at least one (e.g., at least 2, at least 3, at least 5, at least 10, at least 15, or at least 20) and/or at most 30 (e.g., at most 25, at most 20, at most 15, at most 10, or at most 5) filtration media 124b.

Without wishing to be bound by theory, it is believed that using a combination of filters 122a and 122b in which filtration media 124a and 124b are made from different materials can maximize the reduction of impurities, particles, and metal ions to obtain an ultra-high pure organic solvent. Further, without wishing to be bound by theory, it is believed that, in embodiments where filtration media 124a are made from a nylon and filtration media 124b are made from a fluoropolymer (e.g., a PTFE) or vice versa, filtration media 124a and 124b can have a relatively larger pore size (e.g., 5 nm) and still have better filtration results than filtration media having a smaller pore size (e.g., 3 nm) but made from different materials (e.g., a polyolefin).

Referring to FIG. 1, second filtration system 120 includes a recirculation conduit 160f to form a recirculation loop for recirculating a partially-purified organic solvent back to storage tank 130 and to be processed by filters 122 in second filtration system 120 again. In some embodiments, the partially-purified organic solvent is recirculated at least two times (e.g., at least three times, at least four times, or at least five times) before the purification process is completed and the organic solvent is transferred to packaging station 140. In some embodiments, without wishing to be bound by theory, it is believed that recirculating the partially-purified solvent through second filtration system 120 more than two times may not achieve further improvement in impurities removal. In the examples as shown in FIG. 1, recirculation conduit 160f is configured at the downstream side of outflow port 120b of second filtration system 120. In other examples, recirculation conduit 160f can be configured at the upstream side of outflow port 120b.

In some embodiments, second filtration system 120 can include one or more optional temperature control unit 180 (e.g., a heat exchanger) at any suitable place. For example, temperature control unit 180 can be configured along the recirculation conduit 160f. In some embodiments, temperature control unit 180 can be configured between supply port 120a and filter 122a, between filter 122a and 122b, and between filter 122b and outflow port 120b. In some embodiments, temperature control unit 180 can be configured at a temperature of at most about 80° F. (e.g., at most about 75° F., at most about 70° F., or at most about 65° F.) and/or at least about 30° F. (e.g., at least about 40° F., at least about 50° F., or at least about 60° F.) so that the temperature of the organic solvent in second filtration system 120 can be maintained at about 80° F. or below.

In some embodiments, each of filters 122a and 122b includes a filter housing having an inner surface that includes a fluoropolymer (e.g., a PTFE, a PFA, or a combination thereof). For example, the fluoropolymer can be a coating formed on the inner surfaces of filters 122a and 122b. In some embodiments, if filter 122a or 122b includes a filtration medium made from a fluoropolymer, the entire filter 122a or 122b can be made from the fluoropolymer. In some embodiments, the inner surfaces of all equipment (including conduits and valves, if any) between filter 122a or 122b and packaging station 140 can include a fluoropolymer. Without wishing to be bound by theory, it is believed that using such equipment (also known as fluoropolymer lined equipment) can significantly reduce re-introduction of impurities (e.g., metal ions or organic impurities) into a purified organic solvent.

In some embodiments, when purification system 10 includes both filters 122a and 122b in second filtration system 120, at least some (e.g., all) of components in the equipment (e.g., a filter, a temperature control unit, a conduit, a valve, a supply port, or an outflow port) used in purification system 10 (other than a fluoropolymer filtration medium) can be made of a material that does not contain fluorine. Examples of such materials include stainless steel (including electropolished or non-electropolished stainless steel). It is believed that such a system can be relatively inexpensive and can reduce manufacturing costs, while still being able to produce an ultra-high pure organic solvent.

In some embodiments, packaging station 140 can be a mobile storage tank (e.g., a tank on a tanker) or a fixed storage tank. In some embodiments, packaging station 140 can be a fluoropolymer lined equipment (e.g., the inner surface of which can include a fluoropolymer such as a PTFE).

The present disclosure also features a method of purifying a solvent (e.g., an organic solvent). In general, the purification method can include passing the solvent through one or more (e.g., two or three) filters in second filtration system 120 (e.g., filter 122a and/or 122b). For example, referring to FIG. 1, an unpurified or pre-processed solvent (i.e., a starting material) can be purified by purification system 10 by passing the solvent from supply unit 20 through filters 112 in first filtration system 110 to be collected in storage tank 130, and passing the solvent from storage tank 130 through filters 122 in second filtration system 120 to packaging station 140. In some embodiments, the purification methods described herein can include recirculating the solvent through the recirculation loop in second filtration system 120 (e.g., through storage tank 130, filters 122, and recirculation conduit 160f) at least one time (e.g., two or three times) before transferring the purified solvent to packaging station 140. In some embodiments, the purification methods described herein can include recirculating the solvent through a recirculation loop in first filtration system 110 (e.g., through filters 112 and recirculation conduit 160h) at least one time (e.g., two or three times) before transferring the partially-purified solvent to storage tank 130.

In some embodiments, the unpurified or pre-processed solvent can include an organic solvent containing a metal element selected from the group consisting of iron (Fe), chromium (Cr), nickel (Ni), and lead (Pb). In some embodiments, the amount of each metal component in the pre-processed solvent ranges from about 0.1 to 1000 mass ppt (e.g., 200 to 1000 mass ppt or 500 to 1000 mass ppt).

Referring to FIG. 1, when the pre-processed solvent reaches a temperature control unit (e.g., unit 100 or any subsequent temperature unit such as units 170 and 180), the temperature of the solvent can be adjusted to a predetermined optimal temperature range (e.g., from 30° F. to 80° F., from 30° F. to 70° F., from 41° F. to 67° F., or from 50° F. to 65° F.). For example, the temperature of the solvent can be adjusted to 70° F., 68.5° F., or 67.5° F. In general, the temperature control unit can maintain or adjust the temperature of a solvent either at a particular location (e.g., before the entry of a filter) in purification system 10 or throughout the entire purification system 10.

When the number of particles and the amount of impurities detected from the purified solvent at the end of the processing by first and second filtration systems 110 and 120 are controlled within the predetermined ranges, an ultra-high purity solvent (e.g., containing 0.1 to 100 mass ppt of a metal component selected from the group of metal elements consisting of iron (Fe), chromium (Cr), nickel (Ni) and lead (Pb)) is produced. Subsequently, the ultra-high purity solvent can be transferred to either packaging station 140 or to a manufacturing process for making a semiconductor article.

In some embodiments, the solvent purified by the methods and systems described herein can have a purity of at least about 99.5% (e.g., at least about 99.9%, at least about 99.95%, at least about 99.99%, at least about 99.995%, or at least about 99.999%). In some embodiments, the solvent purified by the methods and systems described herein can have an on-wafer particle count of at most about 500 (e.g., at most about 450, at most about 400, at most about 350, at most about 300, at most about 250, at most about 200, at most about 150, or at most about 100) on an entire wafer. In some embodiments, the solvent purified by the methods and systems described herein can have an on-wafer metal count (e.g., either a total on-wafer metal count or an on-wafer metal count of a specific metal such as Fe or Ni) of at most about 100 (e.g., at most about 90, at most about 80, at most about 70, at most about 60, at most about 50, at most about 40, at most about 30, at most about 20, or at most about 10) on an entire wafer.

The present disclosure is illustrated in more detail with reference to the following examples, which are for illustrative purposes and should not be construed as limiting the scope of the present disclosure.

EXAMPLES

General Description of OWPC and OWMC Measurements

A solvent sample was collected and then inserted into a wafer coating tool. After a bare wafer was coated with a sample, the wafer was transferred to and inspected by a laser-based inspection system. By using a laser light, the laser-based inspection system detected, counted, recorded the location and sizes each particle on the wafer, at a detection limit of 19 nm. More specifically, counting targets included particles having a size of 19 nm or greater. The data was used to create wafer maps and provide the total on-wafer particle counts (OWPC).

The wafer was then transferred to be inspected by EDX (energy dispersive x-ray). Each particle reported by the laser-based inspection system was inspected by EDX (energy dispersive x-ray) for providing the elemental information. Any particle, which was found to produce any metal signal, was counted as a metal particle. The total number of particles with a metal signature was totalized to report as OWMP (on-wafer metal particle).

General Description of Total Trace Metal Measurement

The total trace metal concentration in each solvent sample was tested using ICP-MS (inductively coupled plasma mass spectrometry (ICP-MS). Using a Fujifilm developed method, each sample was tested for the presence of 26 metal species, the detection limit was metal specific, but the typical detection limits were in the range of 0.00010-0.030 ppb. The concentration of each metal species was then totalized to produce the value shown as total trace metal (ppb).

Example 1

Cyclohexanone was the solvent purified in this example. Referring to FIG. 1, cyclohexanone was purified by using the following four purification systems (i.e., Systems 1-4), each of which included first and second filtration systems 110 and 120. In all of Systems 1-4, first filtration system 110 included a 200 nm polypropylene filter as filter 112a, an ion exchange filter as filter 112b, and a 20 nm nylon filter as filter 112c, but did not include any re-circulation loop. The differences among Systems 1-4 are as follows.

In System 1, second filtration system 120 included a 5 nm nylon filter (i.e., a filter having a plurality of filtration media made from nylon and having an average pore size of 5 nm) as filter 122a and a 3 nm PE filter (i.e., a filter having a plurality of filtration media made from polyethylene and having an average pore size of 3 nm) as filter 122b in a recirculation loop, but did not include any PTFE lined equipment or temperature control unit to control the temperature of the solvent.

In System 2, second filtration system 120 included a 5 nm nylon filter as the only filter (i.e., filter 122a) in a recirculation loop, included PTFE lined equipment (i.e., PTFE lined filter housing and PTFE lined conduit between filter 122a and package station 140), and included temperature control unit 180 along recirculation conduit 160f to control the temperature of the solvent below 80° F.

In System 3, second filtration system 120 included a 5 nm nylon filter as filter 122a and a 5 nm PTFE filter (i.e., a filter having a plurality of filtration media made from PTFE and having an average pore size of 5 nm) as filter 122b in a recirculation loop, included PTFE lined equipment (i.e., PTFE lined filter housings and PTFE lined conduit between filter 122a and package station 140), and included temperature control unit 180 along recirculation conduit 160f to control the temperature of the solvent below 80° F.

In System 4, second filtration system 120 included a 5 nm nylon filter as filter 122a and a 5 nm PTFE filter as filter 122b in a recirculation loop, included stainless steel equipment only (i.e., all equipment being made from stainless steel), and included temperature control unit 180 along recirculation conduit 160f to control the temperature of the solvent below 80° F.

The properties (including on-wafer particle count, total on-wafer metal count, on-wafer iron count, and total trace metal count) of the cyclohexanone purified by Systems 1-4 described above were evaluated and summarized in Table 1 below.

TABLE 1

| Cyclohexanone | System 1 | System 2 | System 3 | System 4 |
|---|---|---|---|---|
| On-wafer particle count | 5000 | 475 | 160 | 150 |
| On-wafer metal count (all) | saturated count | 60 | 1.5 | 3 |
| On-wafer metal count (Fe only) | saturated count | 25 | 0 | 0 |
| Total TM count | 2.357 | 0.13 | 0.13 | 0.13 |

"saturated count" means that there are too many defects for the system to count.

As shown in Table 1, the cyclohexanone purified by System 1 exhibited relatively high on-wafer particle count, total on-wafer metal count, on-wafer iron count, and total trace metal count. Surprisingly, the cyclohexanone purified by System 2, 3, or 4 exhibited significantly lower on-wafer particle count, total on-wafer metal count, on-wafer iron count, and total trace metal count than the cyclohexanone purified by System 1.

Example 2

Ethyl lactate was purified by using Systems 5-7. System 5 was the same as System 1 described in Example 1 except that second filtration system 120 includes only one 5 nm nylon filter. System 6 was the same as System 2 described in Example 1. System 7 was the same as System 3 described in Example 1.

The properties (including on-wafer particle count, total on-wafer metal count, on-wafer iron count, on-wafer nickel count, and total trace metal count) of the ethyl acetate purified by Systems 5-7 were evaluated and summarized in Table 2 below.

TABLE 2

| Ethyl Lactate | System 5 | System 6 | System 7 |
|---|---|---|---|
| On-wafer particle count | 1949 | 350 | 175 |
| On-wafer metals count (all) | 237 | 30 | 10 |
| On-wafer metal count (Fe only) | 35 | 5 | 3 |
| On-wafer metal count (Ni only) | 11 | 0 | 1 |
| Total TM count | 0.7 | 0.4 | 0.13 |

As shown in Table 2, the ethyl acetate purified by System 5 exhibited relatively high on-wafer particle count, total on-wafer metal count, on-wafer iron count, on-wafer nickel count, and total trace metal count. Surprisingly, the ethyl acetate purified by System 6 or 7 exhibited significantly lower on-wafer particle count, total on-wafer metal count, on-wafer iron count, on-wafer nickel count, and total trace metal count than the ethyl acetate purified by System 5.

While the invention has been described in detail with reference to certain embodiments thereof, it will be understood that modifications and variations are within the spirit and scope of that which is described and claimed.

What is claimed is:

1. A method of purifying an organic solvent, comprising:
   passing an organic solvent through a first filter to a packaging station in a purification system to obtain a purified organic solvent, the first filter comprising a filter housing and at least one filtration medium within the filter housing, and the at least one filtration medium having an average pore size of at most about 5 nm;
   wherein the purification system comprises the first filter, the packaging station, and a conduit in fluid communication with the first filter and the packaging station, and the inner surface of the conduit or the filter housing comprises a fluoropolymer.
2. The method of claim 1, further comprising passing the organic solvent through a second filter in fluid communication with and between the first filter and packaging station, wherein the second filter comprises a filter housing and at least one filtration medium within the filter housing, and the at least one filtration medium in the second filter has an average pore size of at most about 5 nm.
3. The method of claim 2, wherein the at least one filtration medium in the first or second filter comprises a polyamide, a polyolefin, a fluoropolymer, or a copolymer thereof.
4. The method of claim 2, wherein the at least one filtration medium in the first or second filter comprises a nylon, a polyethylene, a polytetrafluoroethylene, or a copolymer thereof.
5. The method of claim 2, wherein the at least one filtration medium in the first filter comprises a nylon.
6. The method of claim 2, wherein the at least one filtration medium in the second filter comprises a polytetrafluoroethylene.
7. The method of claim 2, wherein the inner surface of the filter housing of the second filter comprises a fluoropolymer.
8. The method of claim 7, wherein the fluoropolymer in the inner surface of the first filter, the second filter, or the conduit comprises a polytetrafluoroethylene or a copolymer thereof.
9. The method of claim 2, wherein the entire second filter is made of a fluoropolymer.
10. The method of claim 2, wherein the first filter comprises 1 to 120 filtration media, and the second filter comprises 1 to 30 filtration media.
11. The method of claim 1, wherein passing the organic solvent through the first filter to the packaging station is performed at a temperature of at most about 80° F., or wherein the method further comprises passing the organic solvent through a heat exchanger to maintain the temperature of the organic solvent at most about 80° F.
12. The method of claim 1, further comprising passing the organic solvent through a third filter before passing the organic solvent through the first filter, wherein the third filter comprises at least one filtration medium that has an average pore size of at most about 200 nm.
13. The method of claim 12, further comprising passing the organic solvent through a fourth filter after passing the organic solvent through the third filter but before passing the organic solvent through the first filter, wherein the fourth filter comprises at least one ion exchange filtration medium.
14. The method of claim 13, further comprising passing the organic solvent through a fifth filter after passing the organic solvent through the fourth filter but before passing the organic solvent through the first filter, wherein the fifth filter comprises at least one filtration medium that has an average pore size of at most about 20 nm.
15. The method of claim 1, further comprising circulating the organic solvent through a recirculation loop comprising the first filter at least two times before passing the organic solvent to the packaging station.
16. The method of claim 1, wherein the organic solvent comprises cyclohexanone, ethyl lactate, n-butyl acetate, propylene glycol monomethyl ether, propylene glycol monomethyl ether acetate, 4-methyl-2-pentanol, or propylene carbonate.
17. A method of purifying an organic solvent, comprising:
   passing an organic solvent through first and second filters to obtain a purified organic solvent;
   wherein the first filter comprises at least one filtration medium that has an average pore size of at most about 5 nm and comprises a polyamide, and the second filter comprises at least one filtration medium that has an average pore size of at most about 5 nm and comprises a fluoropolymer.
18. The method of claim 17, wherein the polyamide comprises a nylon and the fluoropolymer comprises a polytetrafluoroethylene.

19. The method of claim 17, wherein the entire second filter is made of the fluoropolymer.

20. The method of claim 17, wherein the first filter comprises 1 to 120 filtration media and the at second filter comprises 1 to 30 second filtration media.

21. The method of claim 17, wherein passing the organic solvent is performed at a temperature of at most about 80° F. or wherein the method further comprises passing the organic solvent through a heat exchanger to maintain the organic solvent to the temperature of at most about 80° F.

22. The method of claim 17, wherein the first filter comprises a filter housing and at least one filtration medium within the filter housing, the second filter comprises a filter housing and at least one filtration medium within the filter housing, and the inner surface of the filter housing of the first or second filter comprises a fluoropolymer.

23. The method of claim 17, wherein the first and second filters are in a purification system; the purification system further comprises a packaging station, and a conduit in fluid communication with the first filter, the second filter, and the packaging station; and the inner surface of the conduit comprises a fluoropolymer.

24. The method of claim 17, further comprising passing the organic solvent through a third filter before passing the organic solvent through the first and second filters, wherein the third filter comprises at least one filtration medium that has an average pore size of at most about 200 nm.

25. The method of claim 24, further comprising passing the organic solvent through a fourth filter after passing the organic solvent through the third filter but before passing the organic solvent through the first and second filters, wherein the fourth filter comprises at least one ion exchange filtration medium.

26. The method of claim 25, further comprising passing the organic solvent through a fifth filter after passing the organic solvent through the fourth filter but before passing the organic solvent through the first and second filters, wherein the fifth filter comprises at least one filtration medium that has an average pore size of at most about 20 nm.

27. The method of claim 17, further comprising circulating the organic solvent through a recirculation loop comprising the first and second filters at least two times before passing the organic solvent to a packaging station.

28. The method of claim 17, wherein the organic solvent comprises cyclohexanone, ethyl lactate, n-butyl acetate, propylene glycol monomethyl ether, propylene glycol monomethyl ether acetate, 4-methyl-2-pentanol, or propylene carbonate.

29. A system, comprising:
a first filter, wherein the first filter comprises a filter housing and at least one filtration medium within the filter housing, and the at least one filtration medium has an average pore size of at most about 5 nm;
a packaging station; and
a conduit in fluid communication with the first filter and the packaging station;
wherein the inner surfaces of the filter housing and the conduit comprise a fluoropolymer.

30. A system, comprising:
a first filter, the first filter comprising a filter housing and at least one filtration medium within the filter housing, wherein the at least one filtration medium has an average pore size of at most about 5 nm and comprises a polyamide; and
a second filter in fluid communication with the first filter, the second filter comprising a filter housing and at least one filtration medium within the filter housing, wherein the at least one filtration medium has an average pore size of at most about 5 nm and comprises a fluoropolymer.

* * * * *